(12) United States Patent
Musa

(10) Patent No.: US 6,590,018 B2
(45) Date of Patent: Jul. 8, 2003

(54) VINYL SILANE COMPOUNDS CONTAINING EPOXY FUNCTIONALITY

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/966,454

(22) Filed: Sep. 28, 2001

(65) Prior Publication Data

US 2003/0083452 A1 May 1, 2003

(51) Int. Cl.$^7$ ................................................ C08L 83/00
(52) U.S. Cl. ........................ 524/264; 528/32; 549/215; 549/555; 556/400
(58) Field of Search .......................... 528/32; 549/215, 549/555; 524/264; 556/400

(56) References Cited

U.S. PATENT DOCUMENTS

| 3,770,768 A | 11/1973 | Holub et al. ............ 260/326 R |
| 3,803,196 A | 4/1974 | Holub et al. ......... 260/448.2 N |
| 3,944,707 A | * 3/1976 | Foley et al. |
| 4,876,363 A | 10/1989 | Funahashi et al. |

FOREIGN PATENT DOCUMENTS

| EP | 0 228 775 | 10/1986 |
| JP | 57141447 | 9/1982 |
| JP | 01069607 | 3/1989 |
| JP | 02251556 | 10/1990 |
| JP | 10206861 | 8/1998 |

OTHER PUBLICATIONS

Andrianov, XP 002225783 Chemical Abstracts, vol. 50, No. 11, 1956, Columbus, Ohio, US; abstract No. 14517d.*
Ready, Thomas E.: "Facile and Effective Synthesis of Siloxane–Based Polyamines", Macromol. Rapid Commun. 2001, 22, 654–657.
Search Results ACS Registry—(9 Pages).
Search Results ACS Registry—(12 Pages).

* cited by examiner

Primary Examiner—Robert Dawson
Assistant Examiner—Kuo-Liang Peng
(74) Attorney, Agent, or Firm—Jane E. Gennaro

(57) ABSTRACT

Compounds containing vinyl silane and epoxy functionality can be used as adhesion promoters or the main resin in curable compositions.

2 Claims, No Drawings

VINYL SILANE COMPOUNDS CONTAINING EPOXY FUNCTIONALITY

FIELD OF THE INVENTION

This invention relates to compounds that contain both vinyl silane functionality and epoxy functionality and that can be used as adhesion promoters or curable compositions.

BACKGROUND OF THE INVENTION

Adhesive compositions are used in the fabrication and assembly of semiconductor packages and microelectronic devices, such as in the bonding of integrated circuit chips to lead frames or other substrates, and the bonding of circuit packages or assemblies to printed wire boards. Lead frames can be fabricated of 42Fe/58Ni alloy (Alloy 42), copper, or silver- or palladium-coated copper, and wire boards of ceramic or laminate, and adhesives that in general have good performance may be deficient when used on one or more of these substrates.

The addition of adhesion promoters to the adhesive compositions or the use of curable resins that contain adhesion promoting capability as the adhesive would serve to correct this deficiency.

SUMMARY OF THE INVENTION

In one embodiment, this invention relates to compounds that contain both vinyl silane functionality and epoxy functionality. In another embodiment, this invention is a curable composition, such as an adhesive, coating, or encapsulant composition, containing those compounds.

DETAILED DESCRIPTION OF THE INVENTION

The compounds of this invention contain at least one epoxy functionality and at least one vinyl silane functionality. In general, these compounds can be prepared by the reaction of a glycidol or a glycidyl ether polyol with a vinyl silane. Suitable vinyl silanes include trivinylchlorosilane, methyl vinyl dichlorosilane, diphenyl vinyl chlorosilane and vinyl trichlorosilane.

In another embodiment, this invention is a curable composition, such as an adhesive, coating, encapsulant or sealant, containing the inventive compounds. The curable composition can be in the form of a paste prepared by standard blending or milling techniques, or can be a film prepared by film forming techniques as known in the art. The curable composition will include optionally a curing agent, and optionally a filler.

The inventive epoxy/vinyl silane compounds can be the main component in the curable composition or can be added as an adhesion promoter to another curable resin. When used as an adhesion promoter, the amount of the epoxy/vinyl silane compound used in the curable composition will be an effective amount to promote adhesion and, in general, an effective amount will range from 0.005 to 20.0 percent by weight of the formulation.

Examples of curable resins for use as the main component other than the inventive vinyl silanes include epoxies, electron donor resins (for example, vinyl ethers, thiol-enes, and resins that contain carbon to carbon double bonds attached to an aromatic ring and conjugated with the unsaturation in the aromatic ring, such as compounds derived from cinnamyl and styrenic starting compounds), and, electron acceptor resins (for example, fumarates, maleates, acrylates, and maleimides).

Suitable curing agents are thermal initiators and photoinitiators present in an effective amount to cure the composition. In general, those amounts will range from 0.5% to 30%, preferably 1% to 20%, by weight of the total organic material (that is, excluding any inorganic fillers) in the composition. Preferred thermal initiators include peroxides, such as butyl peroctoates and dicumyl peroxide, and azo compounds, such as 2,2'-azobis(2-methyl-propanenitrile) and 2,2'-azobis(2-methyl-butanenitrile). A preferred series of photoinitiators is one sold under the trademark Irgacure by Ciba Specialty Chemicals. In some formulations, both thermal initiation and photoinitiation may be desirable: the curing process can be started either by irradiation, followed by heat, or can be started by heat, followed by irradiation. In general, the curable compositions will cure within a temperature range of 70° C. to 250° C., and curing will be effected within a range of ten seconds to three hours. The actual cure profile will vary with the components and can be determined without undue experimentation by the practitioner.

The formulations may also comprise nonconductive or thermally or electrically conductive fillers. Suitable conductive fillers are carbon black, graphite, gold, silver, copper, platinum, palladium, nickel, aluminum, silicon carbide, boron nitride, diamond, and alumina. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoro-ethylene, vinylidene fluoride, vinyl fluoride, vinylidene chloride, and vinyl chloride. If present, fillers generally will be in amounts of 20% to 90% by weight of the formulation.

The following Examples disclose a synthetic procedure used to make the vinyl silane/epoxy compounds disclosed in this specification, and the performance of representative samples in curable compositions.

EXAMPLES

Example 1.

General Synthetic Procedure: Reaction of alcohol with vinyl silane. One mole equivalent of alcohol and triethylamine are mixed in dry toluene at 0° C., to which is added one mole equivalent of vinyl silane dissolved in toluene. The mixture is allowed to react for four hours at room temperature, after which the solvent is evaporated to give the product.

Example 2.

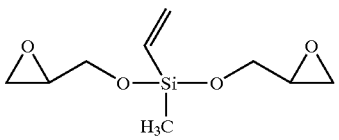

To a 250 mL round bottle flask was added glycidol (10.50 g, 0.142 mole), triethylamine (20 mL) and toluene (50 mL). Methyl vinyl dichlorosilane (10.00 g, 0.07 mole) was added dropwise at 0° C. (performed in an ice bath) through a slow-add funnel. After addition was completed, the ice bath was removed and the mixture was stirred at room temperature for four hours. The mixture was filtered and the filtrate charged to a 250 mL round bottle flask. The solvent was removed under reduced pressure to give the product in 85% yield.

Example 3.

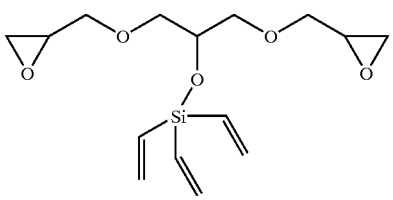

To a 250 mL round bottle flask was added glycerol diglycidyl ether (14.11 g, 0.07 mole), triethylamine (6.98 g, 0.07 mole) and toluene (50 mL). Trivinyl chlorosilane (10.00 g, 0.07 mole) was added dropwise at 0° C. (performed in an ice bath) through a slow-add funnel. After addition was completed, the ice bath was removed and the mixture stirred at room temperature for four hours. The mixture was then filtered and the filtrate charged to a 250 mL round bottle flask. The solvent was removed under reduced pressure to give the product in 85% yield.

Example 4.

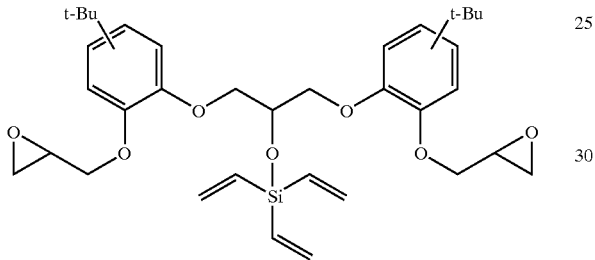

To a 250 mL round bottle flask was added EPICLON EXA-7120 (34.48 g, 0.07 mole), triethylamine (6.98 g, 0.07 mole) and toluene (50 mL). Trivinyl chlorosilane (10.00 g, 0.07 mole) was added dropwise at 0° C. (performed in an ice bath) through a slow-add funnel. Once addition was completed, the ice bath was removed and the mixture stirred at room temperature for four hours. The mixture was filtered and the filtrate charged to a 250 mL round bottle flask. The solvent was removed under reduced pressure to give the product in 90% yield.

Example 5.

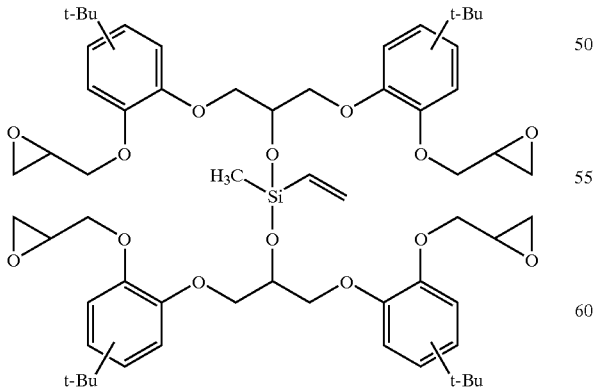

in which t-Bu stands for a tertiary butyl group. To a 250 mL round bottle flask was added EPICLON EXA-7120 (34.48 g, 0.07 mole), triethylamine (7.34 g, 0.073 mole) and toluene (50 mL). Methyl vinyl dichlorosilane (4.88 g, 0.035 mole) was added dropwise at 0° C. (performed in an ice bath) through a slow-add funnel. Once addition was completed, the ice bath was removed and the mixture was stirred at room temperature for four hours. The mixture was filtered and the filtrate charged to a 250 mL round bottle flask. The solvent was removed under reduced pressure to give the product in 90% yield.

Example 6.

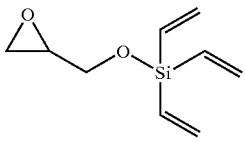

This compound is prepared according to the general synthetic procedure in Example 1 by the reaction of glycidol with trivinyl chlorosilane.

Example 7.

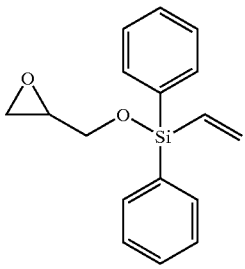

This compound is prepared according to the general synthetic procedure in Example 1 by the reaction of glycidol with diphenyl vinyl chlorosilane.

Example 8.

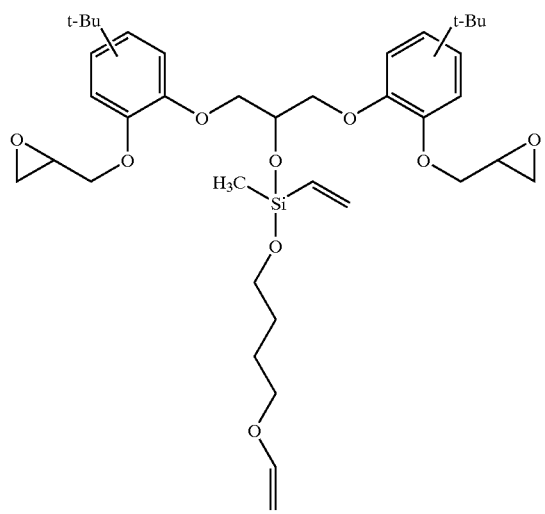

This compound is prepared according to the general synthetic procedure in Example 1 by the reaction of EPICLON EXA-7120 with methyl vinyl dichlorosilane, followed by reaction with 1,4-butanediol vinyl ether according to the general synthetic procedure in Example 1.

Example 9.

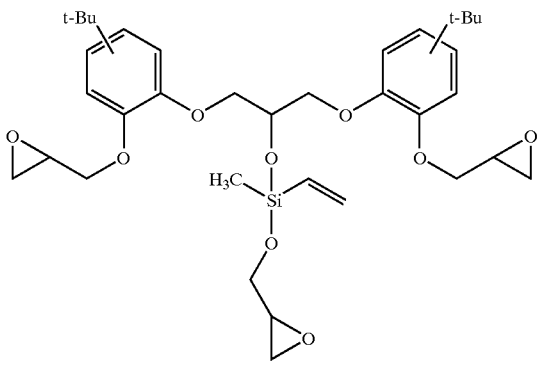

This compound is prepared according to the general synthetic procedure in Example 1 by the reaction of EPICLON EXA-7120 with methyl vinyl dichlorosilane, followed by reaction with glycidol according to the general synthetic procedure in Example 1.

Example 10.

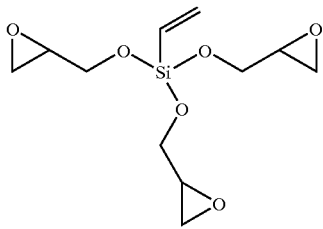

This compound is prepared according to the procedure in Example 1 by the reaction of glycidol with vinyltrichlorosilane.

Example 11.

Performance in curable compositions. A curable composition was prepared comprising a bismaleimide, a compound with styrenic functionality, an epoxy, curing agents, and 75% by weight silver. Vinyl silane/epoxy compounds from Examples 2, 3, 4, and 5 were added to this composition at 1 weight % and the individual curable compositions tested for adhesive strength as die attach adhesives.

The adhesive was dispensed on a silver coated leadframe, a silicon die (120×1200 mil) was placed onto the adhesive, and the adhesive was cured on a hot plate at 200° C. for 60 seconds. Ten assemblies for each adhesive were prepared. Each die was sheared from the leadframe at 90 degrees with a Dage 2400-PC Die Shear Tester at 240° C., and the results pooled and averaged and reported as Kilogram force.

The results are set out in the following table and show that the addition of the vinyl silane/epoxy compounds to the curable composition improved adhesion on silver leadframes over the curable composition without the vinyl silane/epoxy compounds. The compound from Example 3 in a curable composition also gave improved results on a copper leadframe.

| Vinyl Silane/Epoxy | Die Shear Strength at 240° C. in KgF |
|---|---|
| None | 0.7 |
| Compound from Ex. 2 | 1.4 |
| Compound from Ex. 3 | 2.2 |
| Compound from Ex. 4 | 1.9 |
| Compound from Ex. 5 | 1.8 |

What is claimed:

1. A compound having at least one epoxy functionality and one vinyl silane functionality per molecule selected from te group consisting of:

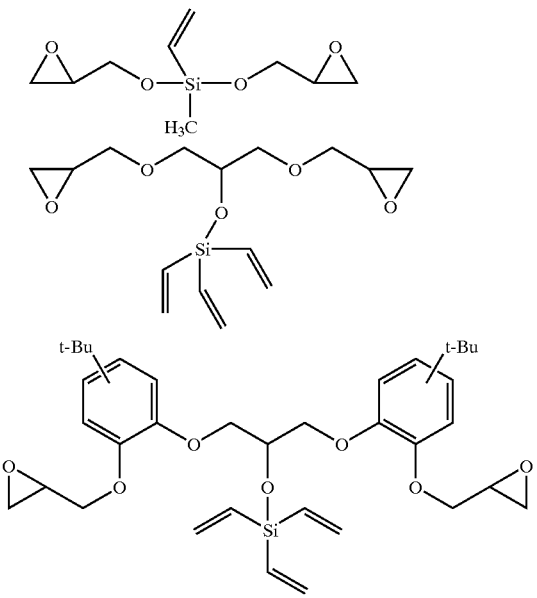

and

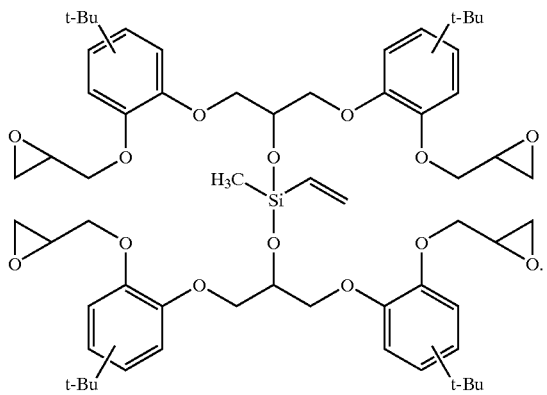

2. A curable composition comprising a compound having at least one epoxy functionality and one vinyl silane functionality per molecule selected from the group consisting of

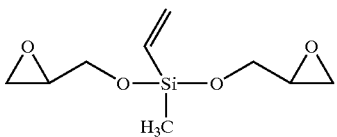

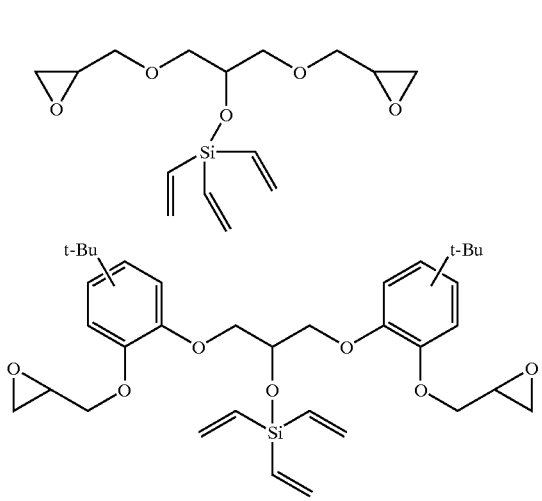
and
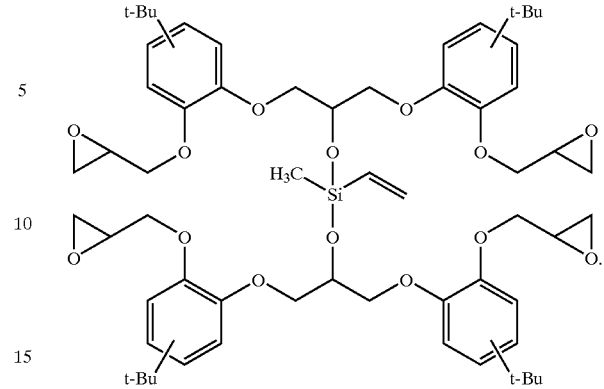
and a curing agent and a filler.
* * * * *